(12) United States Patent
Schroeder

(10) Patent No.: US 8,093,208 B2
(45) Date of Patent: Jan. 10, 2012

(54) THERAPEUTIC PEPTIDES FOR THE TREATMENT OF METASTATIC CANCER

(75) Inventor: Joyce A. Schroeder, Tuscon, AZ (US)

(73) Assignee: Arizona Biomedical Research Commission, Phoenix, AZ (US)

( * ) Notice: Subject to any disclaimer, the term of this patent is extended or adjusted under 35 U.S.C. 154(b) by 0 days.

(21) Appl. No.: 12/847,355

(22) Filed: Jul. 30, 2010

(65) Prior Publication Data

US 2010/0291096 A1 Nov. 18, 2010

Related U.S. Application Data

(62) Division of application No. 11/404,959, filed on Apr. 17, 2006, now Pat. No. 7,767,642.

(60) Provisional application No. 60/671,956, filed on Apr. 15, 2005.

(51) Int. Cl.
*A61K 39/395* (2006.01)

(52) U.S. Cl. ............... 514/1.1; 424/139.1; 435/69.7; 530/350

(58) Field of Classification Search ................... None
See application file for complete search history.

(56) References Cited

U.S. PATENT DOCUMENTS

2005/0282744 A1* 12/2005 Hollingsworth et al. ....... 514/12

FOREIGN PATENT DOCUMENTS

| WO | 02/058450 | 8/2002 |
| WO | 2004/092339 | 10/2004 |

OTHER PUBLICATIONS

J. S. Wadia et al., "Transmembrane Delivery of Protein and Peptide Drugs by TAT-Mediated Transduction in the Treatment of Cancer," Advanced Drug Delivery Reviews, Feb. 28, 2005, vol. 57, No. 4, pp. 579-596.
E. L. Snyder et al., "Cell Penetrating Peptides in Drug Delivery," Pharmaceutical Research, Mar. 2004, vol. 21, No. 3, pp. 389-393.
S. R. Schwarze et al., "In Vivo Protein Transduction: Delivery of a Biologically Active Protein into the Mouse," Science, Sep. 3, 1999, vol. 285, No. 5433, pp. 1569-1572.
M. Yamamoto et al., "Interactin of the DF3/MUC1 Breast Carcinoma-Associated Antigen and Beta-Catenin in Cell Adhesion," Journal of Biological Chemistry, May 5, 1997, vol. 272, No. 19, pp. 12492-12494.
Y. Li et al., "The Epidermal Growth Factor Receptor Regulates Interaction of the Human DF3/MUC1 Carcinoma Antigen with c-Src and [Beta]-Catenin," Journal of Biological Chemistry, Sep. 21, 2001, vol. 276, No. 38, pp. 35239-35242.
O. Tetsu et al., "[Beta]-Catenin Regulates Expression of Cyclin D1 in Colon Carcinoma Cells," Nature, Apr. 1, 1999, vol. 398, No. 6726, pp. 422-426.
D. W. Green et al., [Beta]-Catenin Antisense Treatment Decreases [Beta]-Catenin Expression and Tumor Growth Rate in Colon Carcinoma Xenografts, Journal of Surgical Research, 2001, vol. 101, No. 1, pp. 16-20.
EPO Search Report dated Jul. 31, 2009 in Application No. 06758384.9.
G. Dietz et al., "Delivery of Bioactive Molecules into the cell: the Trojan Horse Approach," Mol. Cell. Neurosci. 27 (2004), pp. 85-131.
J. Schroeder et al., "MUC1 Alters β-Catenin-Dependent Tumor and Promotes Cellular Invasion," Oncogene (2003) 22, pp. 1324-1332.
Y. Li et al., "Interaction of Glycogen Synthase Kinase 3β with the DF3/MUC1 Carcinoma-Associated Antigen and β-Catenin," Molecular and Cellular Biology, Dec. 1998, pp. 7216-7224.
T. Madura et al., "Activation of Pho in the Injured Axons Following Spinal Cord Injury," EMBO reports, 2004, No. 4, pp. 412-416, vol. 5.
S. Schwarze et al., "Protein Transduction: Unrestricted Delivery into All Cells?" trends in Cell Biology, Jul. 2000, pp. 290-295, vol. 10.
H. Harada et al., "Antitumor Protein Therapy; Application of the Protein Transduction Domain to the Development of a Protein Drug for Cancer Treatment," Breast Cancer, Jan. 2006, No. 1, pp. 16-26, vol. 13.
H. Noguchi et al., "Protein Transduction Technology; A Novel Therapeutic Perspective," Acta Medical Okayama, 2006, No. 1, pp. 1-11, vol. 60.
S. Console et al., "Antennapedia and HIV Transactivator of Transcription (TAT) 'Protein Transduction Domains' Promote Endocytosis of High Molecular Weight Cargo Upon Binding to Cell Surface Glycosaminoglycans," The Journal of Biological Chemistry, Sep. 12, 2003, No. 37, pp. 35109-35114, vol. 278.
Andrew P. Spicer, et. al., "Delayed Mammary Tumor Progression in Muc-1 Null Mice," The Journal of Biological Chemistry (Dec. 15, 1995), vol. 270, No. 55, pp. 30093-30101.
Merck manual, 2005, section 11, chapter 149.
Bitler et al.; "Intracellular MUC1 peptides inhibit cancer progression."; Clinical Cancer Research: An Official Journal of the American Association for Cancer Research; Jan. 2009; vol. 15, No. 1; pp. 100-109.

* cited by examiner

*Primary Examiner* — Christopher R. Tate
*Assistant Examiner* — Roy Teller
(74) *Attorney, Agent, or Firm* — Banner & Witcoff, Ltd.

(57) ABSTRACT

Interaction between MUC1 and β-catenin can be interrupted using polypeptides or antibodies that specifically bind to the binding site on MUC1. Interruption provides the beneficial effect of inhibiting, reducing, and/or retarding invasiveness and metastasis. Fusion polypeptides and antibodies are provided to achieve a therapeutic effect.

26 Claims, 4 Drawing Sheets

Fig. 2

$$\overset{\&}{\text{S}}\overset{}{\text{T}}\text{DR}\overset{\#}{\text{S}}\text{P}\overset{@}{\text{Y}}\text{EKV}\underline{\text{SAGNGGSSLS}}\text{YTNPAV}$$

(M2)          biotin-SAGNGGSSLSY
(M2p)        biotin-SAGNGGSSLSY-P
(M2E)        biotin-SAGNGGSSLSE
(ME)   biotin-DRSPEEKVSAGNGGSSLSETNPAV

THERAPEUTIC PEPTIDES FOR THE TREATMENT OF METASTATIC CANCER

This application claims the benefit of provisional application Ser. Nos. 60/671,956 filed Apr. 15, 2005, the disclosure of which is expressly incorporated herein.

TECHNICAL FIELD OF THE INVENTION

This invention is related to the area of cancer therapeutics. In particular, it relates to methods of inhibiting, retarding, and reducing metastatic cancer growth.

BACKGROUND OF THE INVENTION

The progression of mammary epithelium from an ordered, hormonal and growth factor-dependent tissue to one of metastatic neoplasia involves many steps. These include a loss of growth control, evasion of apoptosis and senescence, invasion into mesenchyme and subsequent intravasation and extravasation at secondary sites. The ability to invade is a key step in this process, and invasion is largely inhibited by the normal function of adherens junctions. Normally functioning adherens junctions are dependent upon a set of protein interactions that links neighboring cells (via E-cadherin homotypic interactions) and the intracellular actin cytoskeleton (via β-catenin). The tumor antigen MUC1 is a protein that promotes the disregulation of adherens junction proteins by sequestering β-catenin from E-cadherin. This proposal is directed at understanding the functional significance of MUC1/β-catenin interactions in cellular invasion and identifying a mechanism to interrupt these interactions as a means of inhibiting cellular invasion and metastasis.

The protein components of adherens junctions are frequently disregulated in cancer progression. In many breast cancer patients, E-cadherin expression is lost and cells no longer maintain homotypic interactions. Additionally, β-catenin has special significance due to its role not only as a cellular adhesion protein, but also as a proto-oncogene. This function is due to the involvement of β-catenin not only in E-cadherin-mediated cell adhesion, but also its presence in discrete cytoplasmic and nuclear pools, functioning as a vital player in Wnt-mediated signaling and as a nuclear cofactor (Orsulic et al., 1999). In polarized epithelium, β-catenin is a vital connection between adherens junctions and the actin cytoskeleton. Under these normal cellular conditions, any excess β-catenin is degraded through a complex signaling cascade that involves the tumor suppressor APC (adenomatous polyposis coli) (Polakis, 2000). Alternatively, under transforming conditions, excess β-catenin frequently builds up in the cytoplasm of breast cancer tumors and metastases (Schroeder et al., 2003), where it interacts with proteins which compete with E-cadherin for β-catenin binding sites (Polakis, 2000; Sommers, 1996). The most well-studied of these is the interaction between β-catenin and the tcf/lef transcription factors in the nucleus, which results in the transcription of a variety of gene products including c-myc and cyclin D1 (He et al., 1998; Shtutman et al., 1999; Tetsu and McCormick, 1999). In other transformed tissues, including breast cancer, β-catenin is also found interacting with transmembrane proteins, including the erbB receptors and the tumor antigen MUC1 (Li et al., 1998; Yamamoto et al., 1997).

MUC1 is a heavily O-glycosylated protein expressed abundantly in the lactating mammary gland in addition to being overexpressed (by greater than 10 fold) in more than 90% of human breast carcinomas and metastases (Hilkens et al., 1995; Zotter et al., 1988). In the normal mammary gland, MUC1 is expressed mainly on the apical surface of glandular epithelium, while in breast cancer, MUC1 is overexpressed, underglycosylated and apical localization is lost (Hilkens et al., 1995). The cytoplasmic domain contains potential docking sites for SH2 containing proteins, as well as a variety of putative kinase recognition sites and is tyrosine-phosphorylated both in vitro and in vivo (Schroeder et al., 2001, Zrihan-Licht, 1994 #248). MUC1 binds both GSK3β and β-catenin through motifs in the cytoplasmic tail similar to those found in the APC protein. Binding of MUC1 by β-catenin results in a reduction in the binding of β-catenin to E-cadherin in ZR-75-1 breast carcinoma cells (Li et al., 1998; Yamamoto et al., 1997). This could potentially subvert E-cadherin mediated cell adhesion in epithelial cells, promoting cell migration (Li et al., 1998). In fact, reduction of MUC1 in human breast cancer cell lines (ZR-75-1S and YMB-S) through the use of anti-sense oligonucleotides results in an E-cadherin-dependent increase in cellular adhesion (Kondo et al., 1998). Additionally, the analysis of invasive human breast cancer samples showed that MUC1 and β-catenin interactions occur in primary tumors, but to an even greater extent in lymph node metastases (Schroeder et al., 2003). Studies have shown that the MUC1/β-catenin interaction is dependent upon phosphorylation of MUC1 by the both the c-src kinase (Li et al., 2001b) and Protein Kinase C delta (PKCδ) (Ren et al., 2002). Phosphorylation of MUC1 in this system by c-src or PKCδ results in a decrease in affinity for GSK3β and an increase in binding to β-catenin.

The role of Muc1 in β-catenin-induced breast cancer progression has been genetically verified in the in vivo tumor model, MMTV-Wnt-1. The Wnts are secreted glycoproteins that bind the transmembrane frizzled receptor, resulting in a signaling cascade that inactivates the mechanism for β-catenin degradation (He et al., 1998; Polakis, 2000; Shtutman et al., 1999; Tetsu and McCormick, 1999). This results in significantly higher levels of β-catenin in the cytoplasm and the stochastic formation of unifocal mammary gland tumors in MMTV-Wnt-1 transgenic mice (Tsukamoto et al., 1988). In tumors derived from MMTV-Wnt-1 mice, MUC1 and β-catenin were found to biochemically interact in a tumor specific manner that localized to the cytoplasm and cellular membrane of transformed epithelium. To determine if MUC1 was functionally important in tumor progression in this model, MTV-Wnt-1 transgenic mice were crossed onto a Muc1-null background (Schroeder et al., 2003). Removal of Muc1 from these mice resulted in an almost 50% delay in tumor onset time. In the same study, pulsing invasive breast cancer cell lines with MUC-1 cytoplasmic domain protein fragments was found to increase their invasive capacity. These fragments represented multiple protein-interaction sites and functioned similarly to transfecting the entire MUC1 cytoplasmic tail. Localization experiments determined that these peptides tracked to invading lamellopodia (invadopodia) and colocalized with β-catenin. It was suggested that the association between MUC1 and β-catenin promotes an alternate localization of β-catenin, away from adherens junctions to sites of membrane protrusions. There, the ability of β-catenin to interact with cytoskeleton-modulating proteins promotes their redistribution and promotes cellular invasion. Therefore, when MUC1 complexes with β-catenin, it promotes the novel interaction between β-catenin and invading cell margins, possibly by acting as a scaffolding protein to bring together multiple kinases with the actin cytoskeleton at sites of membrane invasion. This complex formation may not only promote the transition from hyperplasia to neoplasia in non-metastatic disease, but also induce the dynamic changes necessary for metastatic invasion.

Recent studies have demonstrated that MUC1 is an oncogene. Both in vitro and in vivo evidence demonstrates that overexpression of MUC1 (specifically the cytoplasmic tail of MUC1) results in transformation of breast epithelium ((Li et al., 2003) and Schroeder et al., submitted to JBC). When overexpressed in the transgenic mouse (MMTV-MUC1), approximately 60% of multiparous females develop mammary tumors with a long and highly variable latency (Schroeder et al., 2004). Ninety percent of those animals forming primary mammary gland tumors also develop pulmonary metastases. Immunoprecipitation studies between MUC1 and β-catenin determined that these two proteins interact in the tumors, but not the normal mammary glands. This data indicates that MUC1 and β-catenin interactions are not limited to the published MMTV-Wnt-1 model (Schroeder et al., 2003), but also occur in a MUC1-driven model of mammary gland tumorigenesis. Importantly, the MMTV-MUC1 transgenics are metastatic, further potentially implicating this interaction in metastatic breast cancer. Finally, in vitro evidence demonstrates that transfection of rat 3Y1 fibroblasts with MUC1 also results in not only transformation, but a specific complex formation between MUC1 and β-catenin (Li et al., 2003).

The binding site for β-catenin in the MUC1 cytoplasmic domain is surrounded by binding sites for the tyrosine kinases c-src and EGFR and the serine/threonine kinase PKCδ, and interactions between MUC1 and these kinases are increased in breast cancer cell lines and tumor tissues. Furthermore, PKCδ and src-induced phosphorylation of MUC1 promotes MUC1/β-catenin binding (Li et al., 2001). When cells are provided with peptides that mimic this entire domain, MUC1 and β-catenin colocalize in invadopodia of invasive cell lines and cellular invasion increases 5-10 fold (Schroeder et al., 2003). If smaller protein fragments are provided, representing only EGFR or GSK3β binding sites, no changes in cellular invasion or β-catenin localization is observed (Schroeder et al., 2003). These data suggest that the full-length MUC1 cytoplasmic domain acts as a scaffolding protein to promote invasion, by bringing together β-catenin with cellular kinases at invadopodia.

There is a continuing need in the art to develop treatments that are effecting in treating cancer, in particular late stage and metastatic cancers.

SUMMARY OF THE INVENTION

According to a first embodiment of the invention a fusion peptide is provided. The fusion protein has a structure:

A-B-C or C-B-A.

A is a protein transduction domain which enhances translocation of attached macromolecules across cellular membranes. B is a spacer of 0-5 amino acid residues. C is a polypeptide of 6-15 amino acid residues. C comprises all or a portion of PYEKVSAGNGGSSLS (SEQ ID NO: 1), and the portion of C comprises GGSSLS (SEQ ID NO: 2).

According to another embodiment of the invention a fusion peptide is provided which has a structure:

A-B-C or C-B-A.

A is a protein transduction domain which enhances translocation of attached macromolecules across cellular membranes. B is a spacer of 0-5 amino acid residues. C is a polypeptide of 6-15 amino acid residues. C comprises all or a portion of PYEKVSAGNGGSSLS (SEQ ID NO: 1), and the portion of C comprises GGSSLS (SEQ ID NO: 2). Moreover, at least one of said 6-15 amino acid residues is conservatively substituted such that an uncharged polar amino acid replaces an uncharged polar amino acid, or a non-polar amino acid replaces a non-polar amino acid residue, or an acidic amino acid replaces an acidic amino acid.

According to yet another embodiment of the invention a fusion peptide is provided which has a structure:

A-B-C or C-B-A.

A is a protein transduction domain which enhances translocation of attached macromolecules across cellular membranes. B is a spacer of 0-5 amino acid residues. C is a polypeptide of 6-15 amino acid residues. C comprises all or a portion of PYEKVSAGNGGSSLS (SEQ ID NO: 1), and the portion of C comprises GGSSLS (SEQ ID NO: 2). Moreover, one of said 6-15 amino acid residues is substituted with an A residue.

Another aspect of the invention provides a method of treating a cancer cell. A cancer cell is contacted with a fusion peptide as described above. Invasiveness of the cancer cell is thereby reduced or retarded.

Still another aspect of the invention provides a method of treating a patient with cancer. A fusion peptide as described above is administered to a cancer patient. Invasiveness of the cancer is thereby reduced or retarded.

According to another embodiment of the invention, a method of treating a cancer patient is provided. An antibody which binds to a polypeptide PYEKVSAGNGGSSLS (SEQ ID NO: 1) is administered to the patient. Invasiveness of the cancer is thereby reduced or retarded.

According to still another aspect of the invention a method of producing a polypeptide for treating cancer patients is provided. Cells comprising a vector encoding a polypeptide as described above are cultured under conditions which permit the cells to express the polypeptide. The polypeptide is harvested thereafter from the cells or cell culture medium.

According to a further aspect of the invention a method of treating a cancer patient is provided. A vector encoding a polypeptide as described above is administered to the cancer patient. The polypeptide is thereby expressed and invasiveness of the cancer is thereby reduced or retarded.

These and other embodiments which will be apparent to those of skill in the art upon reading the specification provide the art with new tools for treating cancers, especially metastatic cancer.

BRIEF DESCRIPTION OF THE DRAWINGS

FIG. 2. Peptides designed against the MUC1 cytoplasmic domain. Top sequence (SEQ ID NO: 13) shows MUC1-directed peptide that promote invasion when pulsed into invasive breast cancer cell lines (Schroeder et al., 2003). Residues phosphorylated by PKCδ (*), GSK3β (#), src and EGFR (@) are highlighted (Ren et al., 2002). The sequence known to interact with β-catenin is underlined. Mimetic peptides designed to inhibit MUC1/β-catenin interactions are listed (M2, M2p, M2E, and ME; SEQ ID NO: 7, 7, 8, and 14), with phosphorylated residues (M2P, -P) and tyrosine substitutions to glutamic acid shown (M2E and ME).

FIGS. 3B and 3C show overall levels of β-catenin and Muc1 in these tissues.

DETAILED DESCRIPTION OF THE INVENTION

Figure 1:
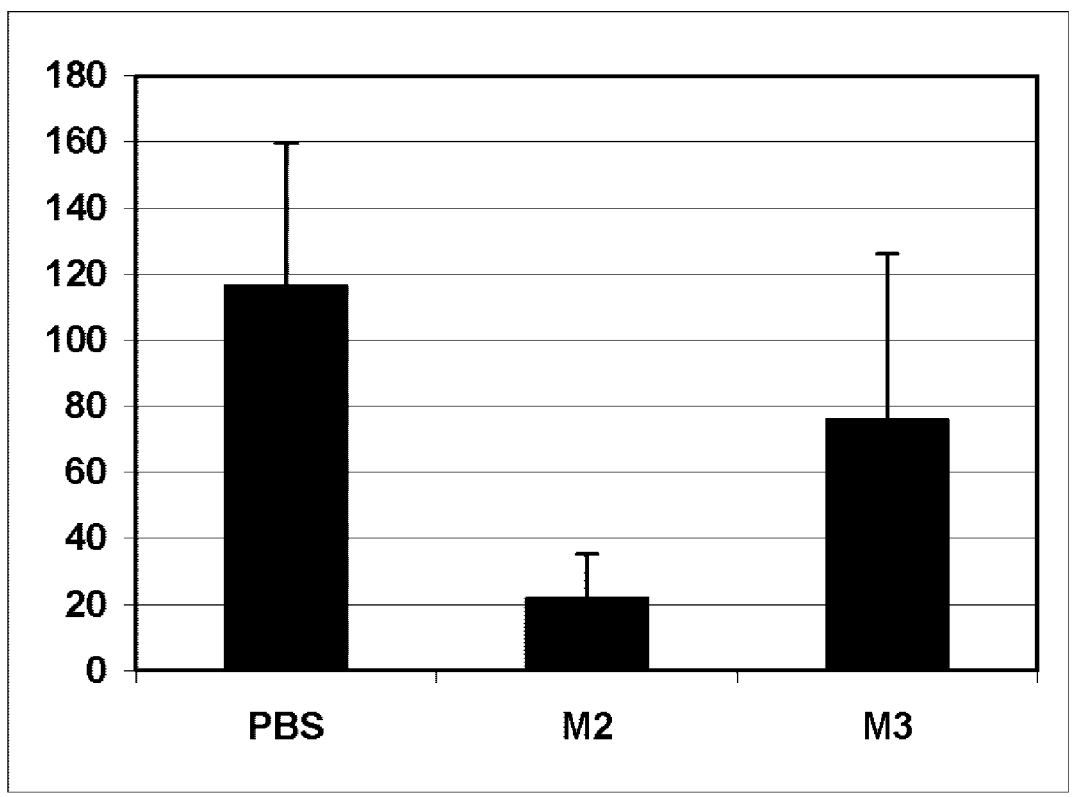
FIG. 1. M2 peptide (MUC1-β-catenin binding domain) inhibits invasion of MDA-MB-468 breast cancer cells. A collagen gel matrix was poured onto the bottom of 8 uM pore sized-transwell inserts (modified Boyden's chamber), then inverted into 20% FBS. Cells were incubated with 100 ng/ml of peptide (with Bioporter reagent to allow for cellular uptake), then added to the top of the Transwell. Cells (serum-free) were allowed to invade into the gel, the gel was removed and invading cells enumerated.

It is a discovery underlying the present invention that oncogenic MUC1 and β-catenin not only promote cancer invasion, but that by blocking their interaction (using a MUC1-mimetic peptide [MEB]), we can inhibit cancer invasion and metastasis.

Any protein transduction domain can be used in the fusion proteins of the present invention. These include any of the domains which have been previously identified and used for protein transduction. See for example the extensive Table 1 of Dietz and Bahr, *Molecular and Cellular Neuroscience,* 27 (2004) 85-131. Certain of such domains are shown in SEQ ID NO: 3, 4, 5, and 6, but the invention is not limited to the use of these. These domains facilitate the uptake by the cells of the attached peptides.

Spacers according to the invention are additional amino acid residues that are used in fusion proteins typically to facilitate manufacture or synthesis. These can be fairly innocuous and typically are of a length of from 0 to 5 residues. The linkers can be monotonous or mixed residue. The residues can be random or sequences obtained from other proteins or designed for a particular reason.

Although some portions of MUC1 have been found to promote invasion and metastasis, surprisingly, it has now been found that portions of certain lengths and composition actually inhibit invasion and metastasis. As previously demonstrated, MUC1 cytoplasmic domain peptides such as SEQ ID NO: 14 increase invasion of breast cancer cells. Schroeder, 2003. Surprisingly, shorter portions of such peptides actually have the opposite effect. These peptides comprises from 6 to 15 contiguous amino acid residues selected from SEQ ID NO: 1 and include the amino acid sequence shown in SEQ ID NO: 2. Slight deviations from the precise sequence may be used to optimize activity, such as by substitution of one, two or three residues to make conservative changes or by substitution with alanine Conservative changes substitute similar residues for each other, such as an uncharged polar for an uncharged polar, or a non-polar for a non-polar, or an acidic for an acidic residue. Thus G or S residues can be substituted with G, S, T, C, Y, N, and Q. L residues can be substituted with A, V, I, P, F, W, and M. A, V, and P residues can be substituted with A, V, L, I, P, F, W, and M residues. Y or N residues can be substituted with G, S, T, C, Y, N, and Q residues. E residues can be substituted with a D residue. K residues can be substituted with an R or H residue. Any residue can be substituted with an alanine residue unless such substitution is found to destroy the invasion and metastasis inhibiting activity. Such substituted peptides can be readily tested using the invasion assays discussed in the examples.

Cancer cells, in vitro or in vivo, can be contacted with or supplied with the fusion peptides of the present invention. They can be directly supplied as peptides or they can be endogenously produced by supplying the cells with nucleic acid vectors which express and produce the fusion peptides in the cells. For in vivo administration, any delivery technique known in the art can be used, including but not limited to direct intratumoral injection, intramuscular injection, intravascular injection, subcutaneous injection, intraperitoneal injection, etc. In vitro delivery can be accomplished, for example, simply by supplying the fusion peptide to the culture medium.

Cancers and cancer cells which may be treated according to the present invention include breast, ovarian, prostate, cervical, colorectal, lung, brain, head and neck, pancreatic, kidney, and liver. The effect which is observed upon administration is a reduced extent or retarded rate of invasion and metastasis. Suitable assays for measuring these processes are described in the examples. Other assays as are known in the art can be used as well.

Fusion peptides can be formulated or modified as are known in the art. This may involve covalent modifications, such as capping, or PEGylation, or combination with micelles or liposomes. Such modifications and formulations may increase stability in the body, therefore permitting higher percentages of the input dosage to reach the target cancer. The fusion proteins of the present invention can also be used in conjunction with other treatments. The treatments may be administered simultaneously or serially. Other suitable treatments for treating cancers include chemotherapeutic drug administration or infusion, anti-tumor antibodies, anti-receptor antibodies, radiation treatment, radiolabeled drugs, and surgery. Use of two modalities which act in different ways may provide increased benefit to the patient.

A similar inhibitory effect on the binding of MUC1 to β-catenin can be obtained by delivering antibodies to the cell or cancer patient. The antibodies can be any type, monoclonal or polyclonal, single chain or multi-chain. The antibodies may be made in a host mammal, in cell culture, or in recombinant cells. The antibodies bind to an epitope contained in the SEQ ID NO: 1. Antibodies can be raised using a peptide according to SEQ ID NO: 1 as an immunogen, for example, or using fusion proteins according to the invention as immunogens, or using other fusion proteins as immunogens.

Vectors for delivery of nucleic acids encoding the fusion proteins of the present invention can be any that are known in the art. Adenoviral vectors and adeno-associated vectors are will known and widely used. Non-viral vectors can also be used, such as nanoparticles, liposomes, and micelles. Retroviral vectors can be used in some embodiments. The person of skill in the art can select a vector that is suitable for her purposes. Similarly the person of skill in the art can select a vector and host cell system for recombinant manufacture of the fusion proteins of the invention in culture.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Methods

Peptide design: We have designed peptides to the MUC1 cytoplasmic domain that encompass the published binding sites β-catenin (Li et al., 1998; Li et al., 2001a; Li et al., 2001b). Due to the tyrosine phosphorylation of MUC1 by EGFR and c-src, we have designed 25 mer peptides that are both nascent and tyrosine phosphorylated, and will determine the requirement of tyrosine phosphorylation for interaction with β-catenin. Furthermore, we have designed peptides that have the tyrosine residues mutated to glutamic acid residues to determine if this will further inhibit cellular invasion. These peptides will all be synthesized by the American Peptide Company (Sunnyvale, Calif.). The peptides are produced at an 85% purity level (purified by HPLC, assayed by Mass Spectrometry), and biotinylated at the C-terminus for identification purposes.

Peptide treatment and invasion assay: 8 um pore size Transwell inserts (Corning) will be inverted and coated with 90 ul of Type I collagen (rat tail, BD Scientific) gel mixture (2.2% sodium bicarbonate, 10×M199 media), and allowed to solidify for 30 minutes. Wells are then be inverted into DMEM with 20% fetal calf serum and allowed to rehydrate. Peptides are incubated with BioPORTER reagent (Sigma, St. Louis Mo.) for 5 minutes to promote cellular uptake, vortexed, and added to cells in serum-free media (10 ng/ml, 100 ng/ml and ug/ml concentrations will be tested) and placed in the upper chamber of the Transwell. Cells will then be incubated for 2, 4 or 24 hours. Media is removed and gels fixed with 4% paraformaldehyde for 30 minutes and transferred to PBS, pH 7.4. Collagen gels will then either be stained with bizbenzamide for 40 minutes and all cells invaded into a gel enumerated or used in immunofluorescence assays. Invasion of peptide-treated cells are compared to PBS/bioporter treated controls or irrelevant peptide treatment.

Immunoprecipitation and western blotting: Cells pulsed with peptides are allowed to invade into a collagen gel poured in 4-well micro-culture dishes. After invasion, cells are lysed, collagen degraded (via collagenase treatment) and BCA assays (Pierce) performed. Protein lysates are immunoprecipitated as described previously (Schroeder et al., 2003) to determine the level of coprecipitation between endogenous MUC1 and β-catenin, peptides and β-catenin and E-cadherin and β-catenin. Briefly, lysates are either separated by SDS-PAGE and transferred to PVDF membrane directly (Immobilon) or first immunoprecipitated and then separated by SDS-PAGE. Antibodies used for immunoblotting and immunoprecipitation can be obtained from the following sources: anti-Muc1 (Santa Cruz Biochemical) and anti-β-catenin (H-102, immunoprecipitation and C-18, immunoblotting, both from Santa Cruz Biochemical).

Immunofluorescence: Cells undergoing invasion through collagen gels are immunofluorescently labeled in situ (while in the collagen gel). For immunofluorescence on collagen gels, gels are permeabilized with 0.5% Triton X-100 in 10 mM Pipes (pH 6.8), 50 mM NaCl, 300 mM sucrose and 3 mM MgCl$_2$ for 5 minutes at room temperature. Gels are blocked with 3% BSA (Sigma), 0.05% Tween 20, in a 1:1 solution of PBS and Enhancing Wash Buffer (Innovex). Primary antibodies are incubated overnight at 4° C., and gels washed for 6 hours in 1:1 PBS:Enhancing Wash Buffer. Secondary antibodies are incubated overnight at 4° C., and washed again for 6 hours at room temperature. Gels are then mounted, coverslipped and analyzed using a Zeiss laser scanning confocal microscope. The following antibodies are used: anti-biotin (streptavidin-Alexa594, 1:500, Molecular Probes), anti-Muc1 (1:100, Santa Cruz), anti-vinculin (V9131, 1:400, Sigma Chemical Company) anti-β-catenin (H-102, 1:100, Santa Cruz Biochemical), anti-fascin (FCN01, 1:50, Neomarkers), and phalloidin-Alexa546 (1:100, Molecular Probes). Secondary antibodies can be either Alexa 488 or 546 from Molecular Probes.

Peptide tissue targeting: To verify the ability of the peptide to get across the plasma membrane, the peptide is linked to an FITC-tag during synthesis. Peptides are conjugated to the Protein Transduction Domain of the HIV protein TAT (trans-activating transcriptional activator protein), which allow peptides to transverse cell membranes in an endocytosis- and energy-independent way (Torchilin et al., 2001b). Peptide sequences are NH2-FITC-GGG-YARAAARQARA-MUC1peptide-COOH. Peptides are tested on our in vitro system, then either injected intravenously or intraperitoneally. To reduce peptide degradation during whole body delivery, peptides can be conjugated to small micelles or liposomes using modified PEG (Torchilin et al., 2001a; Valero et al., 1999), or subject to end-modifications, such as C-terminal amidation or N-terminal acetylation. Note that in previous studies using the PTD domain of TAT as a peptide tag to β-galactosidase, whole body deliver was obtained with peptides being transduced into most, if not all, tissues in the mouse body (Schwarze et al., 1999).

Animals: To obtain statistically relevant numbers of animals for our study, we utilize 20 animals per treatment arm, which include wild-type, and three optimized dose arms of transgenic animals. We generate additional arms of the study, beginning the treatment at 6 weeks, 8 weeks, and 10 weeks of age to treat animals in early, median and late stage of tumor development for this transgenic model. This results in the use of 180 transgenic and 80 wild-type animals. We test both intraperitoneal and intravenous injection to determine which results in the best delivery.

Histology: Animals are palpated 3 times weekly to monitor tumor growth. When tumor burden has reached 5% of body mass or the animals have reached 16 weeks of age (a time point when ~50% have developed pulmonary metastases), animals are sacrificed. Mammary gland, tumor and lung tissues are harvested and fixed in methacarn or protein lysates are made for analysis. Fixed lungs are analyzed under a dissecting microscope to identify metastatic lesions. We have previously analyzed this method in the MMTV-pyMT model compared to serial sectioning of the lungs and identification of metastasis by hematoxylin and eosin staining (data not shown). We found 100% concordance between the two methods in identifying the lung metastases in this transgenic model.

Immunofluorescence: Tissue sections are analyzed as described previously (Schroeder et al., 2001). Antibodies used for tissue immunofluorescence are as follows: anti-Muc1 (Santa Cruz Biochemical), anti-β-catenin (H-102, 1:500, Santa Cruz Biochemical and A11010-Alexa546, 1:500, Molecular Probes). Tissue sections are paraffin embedded, sectioned and the presence of the fluorescently-tagged peptide determined.

Immunoprecipitation: Protein lysates are produced as described previously (Schroeder et al., 2003). We analyze the various treatment arms to determine if peptide treatments are reducing the ability of β-catenin and MUC1 to form biochemical complexes.

Statistical analysis: We have utilized the Arizona Cancer Center's Biometry Core to determine the number of animals we will need to produce statistically significant results.

Example 2

Effect of MUC1 Expression on Breast Cancer Invasion

To investigate the functional significance of MUC1 expression on breast cancer invasion, we have incubated invasive breast cancer cell lines with MUC1-mimetic peptides designed to the β-catenin interacting domain. We then monitored the effects of peptide treatment on invasion through a filter and into a collagen gel.

We performed initial experiments with these β-catenin-binding site (M2) peptides in MDA-MB-468 cells. Treatment with MUC1/β-catenin (M2) peptides resulted in an approximately 8-fold inhibition of invasion of these cells into a collagen matrix (FIG. 1). We observed less than 15 M2 peptide-treated cells invaded into a collagen matrix in a 4 hour period, compared to approximately 125 cells in PBS controls. A non-specific peptide treatment (M3) gave results similar to PBS treated controls.

Analysis of the binding domains of MUC1 allows us to create a model of protein interactions from these preliminary experiments. For MUC1 to productively bind to β-catenin and promote transformation and invasion, it must first interact with c-src, PLCδ and EGFR kinases (binding domains shown in FIG. 2) (Li et al., 2001b). The M2 peptide represents the β-catenin binding site of MUC1, but contains no sites for interactions with any of the kinases described. If M2 peptide can interact with endogenous β-catenin, it could potentially be preventing endogenous MUC1 from interacting with β-catenin. Therefore, the M2 peptide could be functioning as a dominant negative protein, binding to β-catenin, but preventing it from interacting with intact MUC1 in an invasion-promoting fashion. We have generated additional peptides, both phosphorylated and nascent, in an effort to optimize this inhibition of invasion (FIG. 2). Our design strategy was focused on the minimal interaction domain between Muc1 and β-catenin, while modulating the tyrosine kinase residues in an attempt to determine the functional significance of tyrosine phosphorylation in protein binding.

Example 2

MUC1 and β-Catenin Interact in Mouse Model

Figures 3A, 3B, 3C:
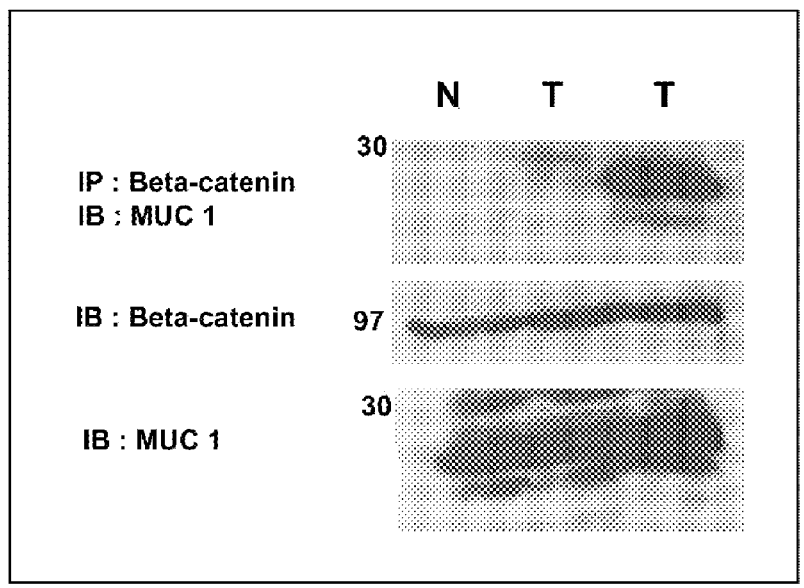
FIGS. 3A-C. Muc1 and β-catenin interact in a tumor-specific manner in MMTV-pyMT transgenic mice. Normal mammary glands and mammary gland tumors from MMTV-pyMT mice were homogenized and protein lysates were immunoprecipitated for β-catenin and immunoblotted for Muc1 (FIG. 3A).
Figure 4:
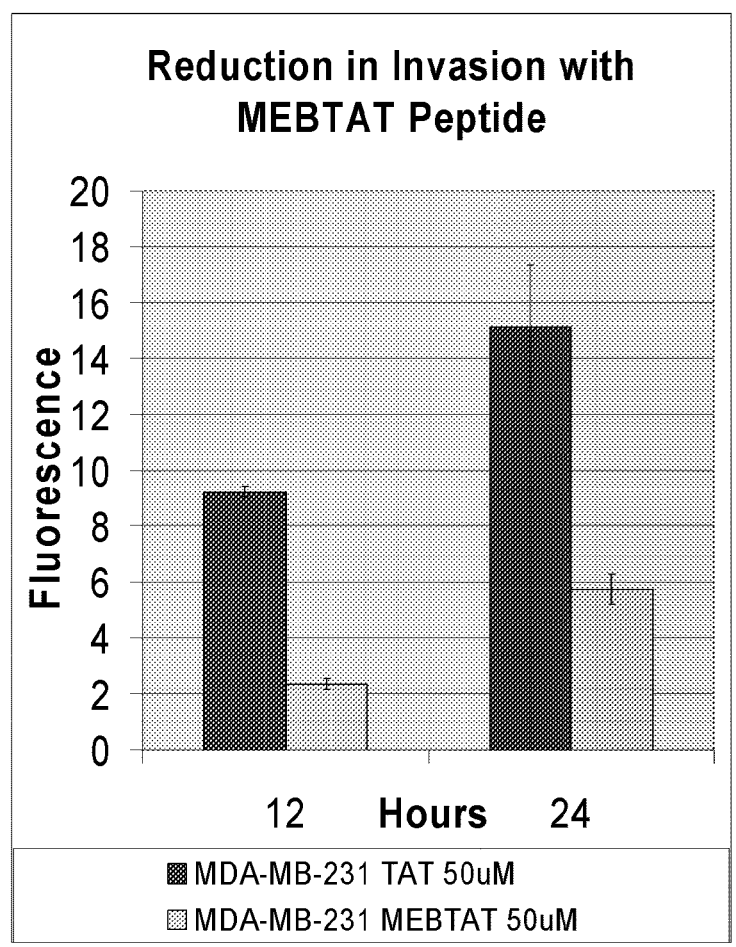
FIG. 4. Treatment of MDA-MB-231 cells with MEBTAT leads to a 5-fold decrease in cell invasiveness as compared to control TAT peptide in invasion assays.

MUC1 and β-catenin interact in a spontaneous model of metastatic breast cancer. While multiple models have demonstrated a tumor-specific interaction between Muc1 and β-catenin (MMTV-Wnt-1, MMTV-MUC1, and breast cancer cell lines), they are not optimal for preclinical models for a variety of reasons (including relevance to human disease, tumor onset and latency). We therefore sought out an additional mouse model that might serve as an appropriate model in which to test our peptide-based therapies. The MMTV-pyMT (Mouse Mammary Tumor Virus—promoter driven Polyoma Middle T antigen) model of breast cancer is a transgenic mouse that develops breast cancer that is metastatic to the lung in greater than 70% of the animals analyzed (Guy et al., 1992a). This is an excellent model of breast cancer progression because it is a) metastatic, b) driven by the pyMT oncogene which interacts with a large number of cellular signaling pathways, including MUC1 (Spicer et al., 1995), c) develops tumors between 12 and 15 weeks of age, making it a good model for drug trials, and d) histologically represents a highly diverse and progressive disease (Maglione et al., 2001). We have examined the interaction between MUC1 and β-catenin in this model and found them to interact in a tumor-specific manner (FIG. 3). While Muc1 and β-catenin are both expressed in normal mammary glands and breast tumors (FIG. 3, bottom 2 panels), we were unable to detect a significant biochemical interaction between the two proteins in the normal gland by immunoprecipitation. Alternatively, a substantial interaction was observed between Muc1 and β-catenin in tumors (FIG. 3, data shown from 2 tumors from different mice, we have repeated this in 7 additional tumors). These data indicate that the interaction between these two proteins is tumor-specific, making this an ideal model to use in our peptide-based therapy. We plan to use this transgenic mouse in our preclinical trials of the inhibitory MUC1-mimetic peptide.

Example 4

TAT-Conjugated MUC1-Mimetic Peptides

We have designed TAT-conjugated MUC1-mimetic peptides for their ability to inhibit the invasion of MDA-MB-231 and MDA-MB-468 invasive breast cancer cell lines. Peptides were designed to carry the TAT transduction domain for entry into cells. The following peptides were designed, produced and tested:

MTAT1 (TAT-SSTDRSPYEKVSAGNGGSSLSYTNP; SEQ ID NO: 12) This peptide represents the MUC1 cytoplasmic domain known to interact with multiple proteins, including β-catenin. This peptide is used for positive controls.

TAT This is the TAT transduction domain, which promotes uptake of the conjugated peptides into the cell. This peptide is used for negative controls.

MBTAT (TAT-SAGNGGSSLS; SEQ ID NO: 9) This peptide represents the β-catenin/MUC1 interaction site, with 4 additional residues surrounding the minimal interaction site.

MB'TAT (TAT-GGSSLS; SEQ ID NO: 2) This peptide represents the minimal reported β-catenin/MUC1 interaction site.

MEBTAT (TAT-PYEKVSAGNGGSSLS; SEQ ID NO: 1) This peptide is the MBTAT peptide with an additional EGFR interaction site.

MTAT1 increased invasion in our assay 18-fold, while MBTAT suppressed invasion 8-fold. This data demonstrates that a full-length MUC1 mimetic peptide can promote cellular invasion, in essence mimicking the affect of endogenous MUC1. Alternatively, the smaller MBTAT peptide blocks invasion, probably by inhibiting the ability of endogenous MUC1 and β-catenin to interact with each other. The MEBTAT blocks invasion of MDA-MB-231 breast cancer cells by 6-fold, and we are investigating whether this is due to blocking the interactions between MUC1 and β-catenin, MUC1 and EGFR, or MUC1 and both β-catenin and EGFR. As previous published data indicate that this interaction between MUC1 and β-catenin is important in breast cancer spread, we are moving forward to use both the MBTAT and the MEBTAT peptides therapeutically in animals.

We use MBTAT and MEBTAT (fluorescently labeled) to treat our transgenic mice. An MMTV-pyMT transgenic mouse is used.

Example 5

Treatment of MDA-MB-231 cells with peptide showed a different localization of β-catenin. TAT control peptide treatment resulted in a disperse localization. MEBTAT peptide treatment resulted in β-catenin localization at sites of focal adhesion and lamellapodia.

Example 6

Trials in Scid Xenograft Model

Trial 1. The MDA-MB-231 cell line was injected (in matrigel) into the mammary fat pad of 24 mice. These mice were then divided into 3 groups and injected once daily, MWF, for 2 weeks.
Group IA was treated (i.p.) with 10 ug/g body weight MEBTAT peptide
Group IB was treated (i.p.) with 20 ug/g body weight MEBTAT peptide
Group IC was treated (i.p.) with 20 ug/g body weight TAT peptide At the end of 2 weeks, we had 27% tumor regression in 1/7 animals in group IA, 7% tumor regression in 1/7 animals in group IB, and no tumor regression (0/7) in group IC. Analysis of tumor volume in all treatment groups demonstrated a 20% decrease in tumor volume in mice treated with MEBTAT compared to TAT.

All tumors were surgically resected 3 days after final drugging, and the mice were monitored for an additional 10 days. Tumors in all 3 groups regrew, with no statistically significant difference in growth rates. There was a difference in the survival rates of the 3 groups as demonstrated by monitoring the percent of animals surviving over time. Analysis of survival found that 100% of the mice in group IA survived until d38 and 100% of the mice in group IB survived until d43, but 100% of the mice in group IC were alive only until d32. This correlates to a 25% increase in overall survival time for the animals taking 20 ug/g body weight of MEBTAT compared to TAT. Importantly, there was no detectable toxicity of the peptide treatment in any of the animals.

Trial II: The MDA-MB-231 cell line was injected (in matrigel) into the mammary fat pad of 16 mice. These mice were then divided into 2 groups and injected once daily, MTWThF, for 2 weeks.

Group IIA was treated (i.v.) with 20 ug/g body weight MEBTAT peptide

Group IIB was treated (i.v.) with 20 ug/g body weight TAT peptide

At the end of 2 weeks, tumor regression was observed in 3/8 of the mice in group IIA (7%, 9%, and 21% tumor volume reduction) and no regression (0/8) of the mice in group IIB. All animals were sacrificed and analyzed for metastases. Visible metastases were seen in 0/8 lungs, 4/8 diaphragms and 1/8 livers of the animals in group IIA. Visible metastases were observed in 0/8 lungs, 4/8 diaphragms and 3/8 livers in group IIB. (Note that lung metastases were not expected due to the early time of sacrifice in this experiment.) There was no detectable toxicity in any of the animals. These data indicated that the MEBTAT peptide treatment may result in a decrease tumor growth and a decrease in distant metastases.

These data indicate that peptide MEBTAT has antitumor and anti-metastatic effects on breast cancer and importantly, shows no toxicity.

Example 7

Invasion Assay of Alanine-Scanning Mutants

The amino acids of the MEB sequence [PYEKVSAG-NGGSSLS; SEQ ID NO: 1] were replaced, one amino acid at a time, with alanine (Note that there are only 14 mutants, as one of the parental amino acid residues. was already an alanine). Note also that this experiment was done one time, with 4 replicas at each data point.

A new assay was performed in a 96-well format. While the suppression of invasion is not as robust as that observed in the 24-well format, we still observe a 3-fold suppression of invasion with MEBTAT treatment over TAT or PBS. Altering amino acids #9 (the N) or #14 (the L) has no apparent effect on the ability of MEBTAT to inhibit invasion. Altering any of the remaining amino acids completely eliminated the effect, indicating a critical role for both the YEKV (EGFR/src binding site) and the SAGNGGSSLS (beta-catenin binding site). Also important is the P (at residue #1) that links MEB to the TAT. The proline could be providing important access of the peptide to MUC1 binding sites.

MDA-MB-231 cells were treated for 1 hour with MEBTAT (M), TAT (T), PBS (P), or alanine scanning mutants of MEBTAT. Cells were treated with Calcein-AM and allowed to invade across an 8-uM Transwell into a Type I collagen gel for 18 hours. Invasion was analyzed by spectrophotometry.

REFERENCES

The disclosure of each reference cited is expressly incorporated herein.

Alpaugh, M. L., Tomlinson, J. S., Kasraeian, S., and Barsky, S. H. (2002). Cooperative role of E-cadherin and sialyl-Lewis X/A-deficient MUC1 in the passive dissemination of tumor emboli in inflammatory breast carcinoma. Oncogene 21, 3631-3643.

Andersen, J. F., Ding, X. D., Balfour, C., Shokhireva, T. K., Champagne, D. E., Walker, F. A., and Montfort, W. R. (2000). Kinetics and equilibria in ligand binding by nitrophorins 1-4: evidence for stabilization of a nitric oxide-ferriheme complex through a ligand-induced conformational trap. Biochemistry 39, 10118-10131.

Bowie, J. U., Reidhaar-Olson, J. F., Lim, W. A., and Sauer, R. T. (1990). Deciphering the message in protein sequences: tolerance to amino acid substitutions. Science 247, 1306-1310.

Brooks, H., Lebleu, B., and Vives, E. (2005). Tat peptide-mediated cellular delivery: back to basics. Adv Drug Deliv Rev 57, 559-577.

Dawson, D. W., Volpert, O. V., Pearce, S. F., Schneider, A. J., Silverstein, R. L., Henkin, J., and Bouck, N. P. (1999). Three distinct D-amino acid substitutions confer potent antiangiogenic activity on an inactive peptide derived from a thrombospondin-1 type 1 repeat. Mol Pharmacol 55, 332-338.

Dietz, G. P., and Bahr, M. (2004). Delivery of bioactive molecules into the cell: the Trojan horse approach. Mol Cell Neurosci 27, 85-131.

Gottlieb, K. A., and Villarreal, L. P. (2001). Natural biology of polyomavirus middle T antigen. Microbiol Mol Biol Rev 65, 288-318; second and third pages, table of contents.

Guy, C. T., Cardiff, R. D., and Muller, W. J. (1992a). Induction of mammary tumors by expression of polyomavirus middle T oncogene: a transgenic mouse model for metastatic disease. Mol Cell Biol 12, 954-961.

Guy, C. T., Webster, M. A., Schaller, M., Parsons, T. J., Cardiff, R. D., and Muller, W. J. (1992b). Expression of the neu protooncogene in the mammary epithelium of transgenic mice induces metastatic disease. Proc Natl Acad Sci USA 89, 10578-10582.

Ha, N. C., Tonozuka, T., Stamos, J. L., Choi, H. J., and Weis, W. I. (2004). Mechanism of phosphorylation-dependent binding of APC to beta-catenin and its role in beta-catenin degradation. Mol Cell 15, 511-521.

He, T. C., Sparks, A. B., Rago, C., Hermeking, H., Zawel, L., da Costa, L. T., Morin, P. J., Vogelstein, B., and Kinzler, K. W. (1998). Identification of c-MYC as a target of the APC pathway. Science 281, 1509-1512.

Hilkens, J., Vos, H. L., Wesseling, J., Boer, M., Storm, J., van der Valk, S., Calafat, J., and Patriarca, C. (1995). Is episialin/MUC1 involved in breast cancer progression? Cancer Lett 90, 27-33.

Ho, A., Schwarze, S. R., Mermelstein, S. J., Waksman, G., and Dowdy, S. F. (2001). Synthetic protein transduction domains: enhanced transduction potential in vitro and in vivo. Cancer Res 61, 474-477.

Hong, F. D., and Clayman, G. L. (2000). Isolation of a peptide for targeted drug delivery into human head and neck solid tumors. Cancer Res 60, 6551-6556.

Huber, A. H., Stewart, D. B., Laurents, D. V., Nelson, W. J., and Weis, W. I. (2001). The cadherin cytoplasmic domain is unstructured in the absence of beta-catenin. A possible mechanism for regulating cadherin turnover. J Biol Chem 276, 12301-12309.

Huber, A. H., and Weis, W. I. (2001). The structure of the beta-catenin/E-cadherin complex and the molecular basis of diverse ligand recognition by beta-catenin. Cell 105, 391-402.

Jimenez, B., Volpert, O. V., Crawford, S. E., Febbraio, M., Silverstein, R. L., and Bouck, N. (2000). Signals leading to apoptosis-dependent inhibition of neovascularization by thrombospondin-1. Nat Med 6, 41-48.

Li, Y., Bharti, A., Chen, D., Gong, J., and Kufe, D. (1998). Interaction of glycogen synthase kinase 3beta with the DF3/MUC1 carcinoma-associated antigen and beta-catenin. Mol Cell Biol 18, 7216-7224.

Li, Y., Kuwahara, H., Ren, J., Wen, G., and Kufe, D. (2001a). The c-Src tyrosine kinase regulates signaling of the human DF3/MUC1 carcinoma-associated antigen with GSK3 beta and beta-catenin. J Biol Chem 276, 6061-6064.

Li, Y., Ren, J., Yu, W., Li, Q., Kuwahara, H., Yin, L., Carraway, K. L., 3rd, and Kufe, D. (2001b). The epidermal growth factor receptor regulates interaction of the human DF3/MUC1 carcinoma antigen with c-Src and beta-catenin. J Biol Chem 276, 35239-35242.

Lilien, J., and Balsamo, J. (2005). The regulation of cadherin-mediated adhesion by tyrosine phosphorylation/dephosphorylation of beta-catenin. Curr Opin Cell Biol 17, 459-465.

Lin, E. Y., Jones, J. G., Li, P., Zhu, L., Whitney, K. D., Muller, W. J., and Pollard, J. W. (2003). Progression to malignancy in the polyoma middle T oncoprotein mouse breast cancer model provides a reliable model for human diseases. Am J Pathol 163, 2113-2126.

Loftin, I. R., Franke, S., Roberts, S. A., Weichsel, A., Heroux, A., Montfort, W. R., Rensing, C., and McEvoy, M. M. (2005). A novel copper-binding fold for the periplasmic copper resistance protein CusF. Biochemistry 44, 10533-10540.

Lopez, J. I., Camenisch, T. D., Stevens, M. V., Sands, B. J., McDonald, J., and Schroeder, J. A. (2005). CD44 attenuates metastatic invasion during breast cancer progression. Cancer Res 65, 6755-6763.

MacDonald, N. J., Shivers, W. Y., Narum, D. L., Plum, S. M., Wingard, J. N., Fuhrmann, S. R., Liang, H., Holland-Linn, J., Chen, D. H., and Sim, B. K. (2001). Endostatin binds tropomyosin. A potential modulator of the antitumor activity of endostatin. J Biol Chem 276, 25190-25196.

Madura, T., Yamashita, T., Kubo, T., Fujitani, M., Hosokawa, K., and Tohyama, M. (2004). Activation of Rho in the injured axons following spinal cord injury. EMBO Rep 5, 412-417.

Maes, E. M., Roberts, S. A., Weichsel, A., and Montfort, W. R. (2005). Ultrahigh Resolution Structures of Nitrophorin 4: Heme Distortion in Ferrous CO and NO Complexes(,). Biochemistry 44, 12690-12699.

Maglione, J. E., Moghanaki, D., Young, L. J., Manner, C. K., Ellies, L. G., Joseph, S. O., Nicholson, B., Cardiff, R. D., and MacLeod, C. L. (2001). Transgenic Polyoma middle-T mice model premalignant mammary disease. Cancer Res 61, 8298-8305.

Morrison, K. L., and Weiss, G. A. (2001). Combinatorial alanine-scanning Curr Opin Chem Biol 5, 302-307.

Parker, B., and Sukumar, S. (2003). Distant metastasis in breast cancer: molecular mechanisms and therapeutic targets. Cancer Biol Ther 2, 14-21.

Piedra, J., Martinez, D., Castano, J., Miravet, S., Dunach, M., and de Herreros, A. G. (2001). Regulation of beta-catenin structure and activity by tyrosine phosphorylation. J Biol Chem 276, 20436-20443.

Polakis, P. (2000). Wnt signaling and cancer. Genes Dev 14, 1837-1851.

Price, J. E., Polyzos, A., Zhang, R. D., and Daniels, L. M. (1990). Tumorigenicity and metastasis of human breast carcinoma cell lines in nude mice. Cancer Res 50, 717-721.

Roberts, S. A., Weichsel, A., Grass, G., Thakali, K., Hazzard, J. T., Tollin, G., Rensing, C., and Montfort, W. R. (2002). Crystal structure and electron transfer kinetics of CueO, a multicopper oxidase required for copper homeostasis in *Escherichia coli*. Proc Natl Acad Sci USA 99, 2766-2771.

Schneider, S. Q., Finnerty, J. R., and Martindale, M. Q. (2003). Protein evolution: structure-function relationships of the oncogene beta-catenin in the evolution of multicellular animals. J Exp Zoolog B Mol Dev Evol 295, 25-44.

Schroeder, J. A., Adriance, M. C., Thompson, M. C., Camenisch, T. D., and Gendler, S. J. (2003). MUC1 alters β-catenin-dependent tumor formation and promotes cellular invasion. Oncogene 22, 1324-1332.

Schroeder, J. A., Al Masri, A., Adriance, M. C., Thompson, M. C., and Gendler, S. J. (2004). Sustained alveolar differentiation accompanies MUC1-induced mammary gland carcinoma and metastasis. Oncogene in press.

Schroeder, J. A., and Lee, D. C. (1998). Dynamic expression and activation of ERBB receptors in the developing mouse mammary gland. Cell Growth Differ 9, 451-464.

Shtutman, M., Zhurinsky, J., Simcha, I., Albanese, C., D'Amico, M., Pestell, R., and Ben-Ze'ev, A. (1999). The cyclin D1 gene is a target of the beta-catenin/LEF-1 pathway. Proc Natl Acad Sci USA 96, 5522-5527.

Spicer, A. P., Rowse, G. J., Lidner, T. K., and Gendler, S. J. (1995). Delayed mammary tumor progression in Muc-1 null mice. J Biol Chem 270, 30093-30101.

Tetsu, O., and McCormick, F. (1999). Beta-catenin regulates expression of cyclin D1 in colon carcinoma cells. Nature 398, 422-426.

Tsukamoto, A. S., Grosschedl, R., Guzman, R. C., Parslow, T., and Varmus, H. E. (1988). Expression of the int-1 gene in transgenic mice is associated with mammary gland hyperplasia and adenocarcinomas in male and female mice. Cell 55, 619-625.

Wadia, J. S., Stan, R. V., and Dowdy, S. F. (2004). Transducible TAT-HA fusogenic peptide enhances escape of TAT-fusion proteins after lipid raft macropinocytosis. Nat Med 10, 310-315.

Webster, M. A., Hutchinson, J. N., Rauh, M. J., Muthuswamy, S. K., Anton, M., Tortorice, C. G., Cardiff, R. D., Graham, F. L., Hassell, J. A., and Muller, W. J. (1998). Requirement for both Shc and phosphatidylinositol 3' kinase signaling pathways in polyomavirus middle T-mediated mammary tumorigenesis. Mol Cell Biol 18, 2344-2359.

Weichsel, A., Andersen, J. F., Roberts, S. A., and Montfort, W. R. (2000). Nitric oxide binding to nitrophorin 4 induces complete distal pocket burial. Nat Struct Biol 7, 551-554.

Weichsel, A., Maes, E. M., Andersen, J. F., Valenzuela, J. G., Shokhireva, T., Walker, F. A., and Montfort, W. R. (2005). Heme-assisted S-nitrosation of a proximal thiolate in a nitric oxide transport protein. Proc Natl Acad Sci USA 102, 594-599.

White, D. E., Kurpios, N. A., Zuo, D., Hassell, J. A., Blaess, S., Mueller, U., and Muller, W. J. (2004). Targeted disruption of beta1-integrin in a transgenic mouse model of human breast cancer reveals an essential role in mammary tumor induction. Cancer Cell 6, 159-170.

Xing, Y., Clements, W. K., Kimelman, D., and Xu, W. (2003). Crystal structure of a beta-catenin/axin complex suggests a mechanism for the beta-catenin destruction complex. Genes Dev 17, 2753-2764.

Xing, Y., Clements, W. K., Le Trong, I., Hinds, T. R., Stenkamp, R., Kimelman, D., and Xu, W. (2004). Crystal structure of a beta-catenin/APC complex reveals a critical role for APC phosphorylation in APC function. Mol Cell 15, 523-533.

Yamamoto, M., Bharti, A., Li, Y., and Kufe, D. (1997). Interaction of the DF3/MUC1 breast carcinoma-associated antigen and beta-catenin in cell adhesion. J Biol Chem 272, 12492-12494.

Zotter, S., Hageman, P. C., Lossnitzer, A., Mooi, W. J., and Hilgers, J. (1988). Tissue and tumor distribution of human polymorphic epithelial mucin. Cancer Reviews 11-12, 55-101.

Zrihan-Licht, S., Baruch, A., Elroy-Stein, O., Keydar, I., and Wreschner, D. H. (1994). Tyrosine phosphorylation of the MUC1 breast cancer membrane proteins. Cytokine receptor-like molecules. FEBS Lett 356, 130-136.

The invention claimed is:

1. A fusion peptide having a structure:

A-B-C or C-B-A wherein A is a protein transduction domain which enhances translocation of attached macromolecules across cellular membranes;
wherein B is a spacer of 0-5 amino acid residues;
wherein C is a polypeptide of 6-15 amino acid residues, wherein C comprises all or a portion of PYEKVSAGNGGSSLS (SEQ ID NO: 1), and wherein the portion of C comprises GGSSLS (SEQ ID NO: 2).

2. The fusion peptide of claim 1 wherein A comprises the protein transduction domain of Human Immunodeficiency Virus TAT protein (SGYGRKKRRQRRRC; SEQ ID NO: 3).

3. The fusion peptide of claim 1 wherein A comprises the protein transduction domain of Antennapedia (SGRQIKIWFQNRRMKWKKC; SEQ ID NO: 4).

4. The fusion peptide of claim 1 wherein A comprises PTD-4 (YARAAARQARA; SEQ ID NO: 5).

5. The fusion peptide of claim 1 wherein A comprises a protein transduction domain of HSV type I protein VP22 (DAATATRGRSAASRPTERPRAPARSASRPRRPVE; SEQ ID NO: 6).

6. The fusion peptide of claim 1 wherein A comprises a copolymer of arginine and lysine.

7. The fusion peptide of claim 1 wherein B comprises glycine-glycine-glycine.

8. The fusion peptide of claim 1 wherein C consists of SAGNGGSSLSY (SEQ ID NO: 7).

9. The fusion peptide of claim 1 wherein C consists of SAGNGGSSLSE (SEQ ID NO: 8).

10. The fusion peptide of claim 1 wherein C consists of SAGNGGSSLS (SEQ ID NO: 9).

11. The fusion peptide of claim 1 wherein C comprises EKVSAGNGGSSLS (SEQ ID NO: 10), but which does not have a residue phosphorylated by PKCδ, GSK3β, SRC, and EGFR.

12. The fusion peptide of claim 1 wherein C consists of SAGNGGSSLSY (SEQ ID NO: 11), wherein the Y residue is phosphorylated.

13. The fusion peptide of claim 1 wherein C consists of PYEKVSAGNGGSSLS (SEQ ID NO: 1).

14. The fusion peptide of claim 1 wherein A is PTD-4 (YARAAARQARA; SEQ ID NO: 5), wherein B is GGG, and wherein C is PYEKVSAGNGGSSLS (SEQ ID NO: 1).

15. A fusion peptide having a structure:

A-B-C or C-B-A wherein A is a protein transduction domain which enhances translocation of attached macromolecules across cellular membranes;
wherein B is a spacer of 0-5 amino acid residues;
wherein C is a polypeptide of 6-15 amino acid residues, wherein C comprises all or a portion of PYEKVSAGNGGSSLS (SEQ ID NO: 1), and wherein the portion of C comprises GGSSLS (SEQ ID NO: 2), wherein one of said 6-15 amino acid residues is conservatively substituted such that an uncharged polar amino acid replaces an uncharged polar amino acid, or a non-polar amino acid replaces a non-polar amino acid residue, or an acidic amino acid replaces an acidic amino acid.

16. The fusion peptide of claim 15 wherein one of said G or S residues of the polypeptide is substituted with an uncharged polar amino acid residue selected from the group consisting of G, S, T, C, Y, N, and Q.

17. The fusion peptide of claim 15 wherein one of said L residues is substituted with a non-polar amino acid residue selected from the group consisting of A, V, I, P, F, W, and M.

18. The fusion peptide of claim 15 wherein one of said A, V, and P residues is substituted with a non-polar amino acid residue selected from the group consisting of A, V, L, I, P, F, W, and M.

19. The fusion peptide of claim 15 wherein one of said Y or N residues is substituted with an uncharged polar residue selected from the group consisting of G, S, T, C, Y, N, and Q.

20. The fusion peptide of claim 15 wherein said E residue is substituted with a D residue.

21. The fusion peptide of claim 15 wherein said K residue is substituted with an R or H residue.

22. A fusion peptide having a structure:

A-B-C or C-B-A wherein A is a protein transduction domain which enhances translocation of attached macromolecules across cellular membranes;

wherein B is a spacer of 0-5 amino acid residues;
wherein C is a polypeptide of 6-15 amino acid residues, wherein C comprises all or a portion of PYEKVSAG-NGGSSLS (SEQ ID NO: 1), and wherein the portion of C comprises GGSSLS (SEQ ID NO: 2) wherein one of said 6-15 amino acid residues is substituted with an A residue.

23. A method of producing a polypeptide for treating cancer patients, comprising:
culturing cells comprising a vector encoding a fusion polypeptide having a structure:

A-B-C or C-B-A under conditions whereby said cells express the polypeptide,
wherein A is a protein transduction domain which enhances translocation of attached macromolecules across cellular membranes;
wherein B is a spacer of 0-5 amino acid residues;
wherein C is a polypeptide of 6-15 amino acid residues, wherein C comprises all or a portion of PYEKVSAG-NGGSSLS (SEQ ID NO: 1), and wherein the portion of C comprises GGSSLS (SEQ ID NO: 2), wherein one of said 6-15 amino acid residues is conservatively substituted such that an uncharged polar amino acid replaces an uncharged polar amino acid, or a non-polar amino acid replaces a non-polar amino acid residue, or an acidic amino acid replaces an acidic amino acid, or wherein one of said 6-15 amino acid residues is substituted with an A residue; and
harvesting the polypeptide from the cells or cell culture medium.

24. The fusion peptide of claim 22 wherein the N residue at position 9 of SEQ ID NO: 1 is substituted with an A residue.

25. The fusion peptide of claim 22 wherein the L residue at position 14 of SEQ ID NO: 1 is substituted with an A residue.

26. A method of producing a polypeptide for treating cancer patients, comprising:
culturing cells comprising a vector encoding a fusion polypeptide having a structure:

A-B-C or C-B-A under conditions whereby said cells express the polypeptide,
wherein A is a protein transduction domain which enhances translocation of attached macromolecules across cellular membranes;
wherein B is a spacer of 0-5 amino acid residues;
wherein C is a polypeptide of 6-15 amino acid residues, wherein C comprises all or a portion of PYEKVSAG-NGGSSLS (SEQ ID NO: 1), and wherein the portion of C comprises GGSSLS (SEQ ID NO: 2); and
harvesting the polypeptide from the cells or cell culture medium.

* * * * *

SEQUENCE LISTING

```
<160> NUMBER OF SEQ ID NOS: 14

<210> SEQ ID NO 1
<211> LENGTH: 15
<212> TYPE: PRT
<213> ORGANISM: Homo sapiens

<400> SEQUENCE: 1

Pro Tyr Glu Lys Val Ser Ala Gly Asn Gly Gly Ser Ser Leu Ser
 1               5                   10                  15

<210> SEQ ID NO 2
<211> LENGTH: 6
<212> TYPE: PRT
<213> ORGANISM: Homo sapiens

<400> SEQUENCE: 2

Gly Gly Ser Ser Leu Ser
 1               5

<210> SEQ ID NO 3
<211> LENGTH: 14
<212> TYPE: PRT
<213> ORGANISM: Homo sapiens

<400> SEQUENCE: 3

Ser Gly Tyr Gly Arg Lys Lys Arg Arg Gln Arg Arg Arg Cys
 1               5                   10

<210> SEQ ID NO 4
<211> LENGTH: 19
<212> TYPE: PRT
<213> ORGANISM: Homo sapiens

<400> SEQUENCE: 4

Ser Gly Arg Gln Ile Lys Ile Trp Phe Gln Asn Arg Arg Met Lys Trp
 1               5                   10                  15

Lys Lys Cys

<210> SEQ ID NO 5
<211> LENGTH: 11
<212> TYPE: PRT
<213> ORGANISM: Homo sapiens

<400> SEQUENCE: 5

Tyr Ala Arg Ala Ala Ala Arg Gln Ala Arg Ala
 1               5                   10

<210> SEQ ID NO 6
<211> LENGTH: 34
<212> TYPE: PRT
<213> ORGANISM: Homo sapiens

<400> SEQUENCE: 6
```

```
Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu
```

<210> SEQ ID NO 7
<211> LENGTH: 11
<212> TYPE: PRT
<213> ORGANISM: Homo sapiens

<400> SEQUENCE: 7

```
Ser Ala Gly Asn Gly Gly Ser Ser Leu Ser Tyr
1               5                   10
```

<210> SEQ ID NO 8
<211> LENGTH: 11
<212> TYPE: PRT
<213> ORGANISM: Homo sapiens

<400> SEQUENCE: 8

```
Ser Ala Gly Asn Gly Gly Ser Ser Leu Ser Glu
1               5                   10
```

<210> SEQ ID NO 9
<211> LENGTH: 10
<212> TYPE: PRT
<213> ORGANISM: Homo sapiens

<400> SEQUENCE: 9

```
Ser Ala Gly Asn Gly Gly Ser Ser Leu Ser
1               5                   10
```

<210> SEQ ID NO 10
<211> LENGTH: 13
<212> TYPE: PRT
<213> ORGANISM: Homo sapiens

<400> SEQUENCE: 10

```
Glu Lys Val Ser Ala Gly Asn Gly Gly Ser Ser Leu Ser
1               5                   10
```

<210> SEQ ID NO 11
<211> LENGTH: 11
<212> TYPE: PRT
<213> ORGANISM: Homo sapiens

<400> SEQUENCE: 11

```
Ser Ala Gly Asn Gly Gly Ser Ser Leu Ser Tyr
1               5                   10
```

<210> SEQ ID NO 12
<211> LENGTH: 25
<212> TYPE: PRT
<213> ORGANISM: Homo sapiens

<400> SEQUENCE: 12

```
Ser Ser Thr Asp Arg Ser Pro Tyr Glu Lys Val Ser Ala Gly Asn Gly
1               5                   10                  15

Gly Ser Ser Leu Ser Tyr Thr Asn Pro
            20                  25
```

<210> SEQ ID NO 13

```
<211> LENGTH: 26
<212> TYPE: PRT
<213> ORGANISM: Homo sapiens

<400> SEQUENCE: 13

Ser Thr Asp Arg Ser Pro Tyr Glu Lys Val Ser Ala Gly Asn Gly Gly
1               5                   10                  15

Ser Ser Leu Ser Tyr Thr Asn Pro Ala Val
            20                  25

<210> SEQ ID NO 14
<211> LENGTH: 24
<212> TYPE: PRT
<213> ORGANISM: Homo sapiens

<400> SEQUENCE: 14

Asp Arg Ser Pro Glu Glu Lys Val Ser Ala Gly Asn Gly Gly Ser Ser
1               5                   10                  15

Leu Ser Tyr Thr Asn Pro Ala Val
            20
```